United States Patent

Racz

[11] Patent Number: 6,066,165
[45] Date of Patent: May 23, 2000

[54] MEDICAL LEAD WITH SIGMA FEATURE

[76] Inventor: Gabor B Racz, 4512 13th St., Lubbock, Tex. 79416

[21] Appl. No.: 09/070,167

[22] Filed: Apr. 30, 1998

[51] Int. Cl.[7] .................................................. A61N 1/05
[52] U.S. Cl. ............................................. 607/117
[58] Field of Search ............................................. 607/117

[56] References Cited

U.S. PATENT DOCUMENTS

| | | | |
|---|---|---|---|
| 4,044,774 | 8/1977 | Corbin et al. | 128/404 |
| 4,379,462 | 4/1983 | Borkan et al. | 128/786 |
| 4,734,527 | 2/1983 | Iverson . | |
| 5,121,754 | 6/1992 | Mullett | 128/786 |

FOREIGN PATENT DOCUMENTS

| | | | |
|---|---|---|---|
| 2431295 | 2/1980 | France | A61N 1/04 |
| WO 99/11320 | 3/1999 | WIPO | A61N 1/05 |

*Primary Examiner*—William E. Kamm
*Attorney, Agent, or Firm*—Banner & Witcoff, Ltd.

[57] ABSTRACT

An implantable medical lead for spinal cord, peripheral nerve or deep brain stimulation comprises a lead body which includes a deformable sigma segment preferably in the shape of a sine wave and a lead paddle coupled to the lead body at the distal end thereof. The lead body at its proximal end may be coupled to an implantable pulse generator, additional, intermediate wiring or other stimulation device. The lead paddle may comprise a plurality of electrode contacts for providing electrical stimulation to targeted human tissue. The lead body, which defines the sigma segment, in a plane, couples the lead paddle and pulse generator. The sigma segment provides flexing and bending of the wire when a patient shifts or moves, and especially provides longitudinal extension between the pulse generator and lead paddle.

14 Claims, 1 Drawing Sheet

MEDICAL LEAD WITH SIGMA FEATURE

BACKGROUND OF THE INVENTION

1. Field of the Invention

The present invention relates to implantable medical stimulators and more particularly to medical leads having a plurality of electrode contacts.

2. Description of the Related Art

Electrical stimulation of electrically excitable tissue such as the brain and/or nerve tissue of the spinal cord can result in pain reduction and/or elimination for the living organism having the stimulated electrically excitable tissue. Thus, for example, medical leads having electrode contacts have been implanted near the spinal column of the human body to provide pain relief for the chronic intractable pain.

Medical leads, which comprise electrode contacts and lead bodies, have been developed to conduct electrical stimulation signals from implantable pulse generators to targeted nerve fibers. These medical leads may be percutaneous leads with the electrode contacts spaced along the lead body. Also, the medical leads may be surgical leads with electrode contacts spaced in an array on a lead paddle. A percutaneously insertable medical lead within a human for applying electrical stimulation to the spinal cord is discussed in U.S. Pat. No. 4,044,774 issued to Corbin et al., and herein is incorporated by reference.

Historically, a straight wire lead body had been used between a medical lead paddle having the electrode contacts and the implantable pulse generator, both of which have been anchored to surrounding tissue. Problems arose using straight wire lead bodies because the straight wire is inelastic and has shorter flex life. As a result of this inelasticity and more limited flex life, when a patient with an implanted medical stimulator and medical lead moves or bends, a straight wire lead body becomes taut and pulls on or places a load on the electrode contacts or the pulse generator or both. Specifically, patient movement tugs or pulls on the wire connection to the electrode contacts of the lead paddle or the wire connection to the implantable pulse generator or both. One solution to this problem has been to coil the wire conductors in the lead body so that the lead body stretches or flexes when the patient moves or shifts around. However, the coiled wire in the lead body disadvantageously increases electrical resistance, sometimes up to three times the electrical resistance in a straight wire lead body. Moreover, when multiple coiled wire conductors are used in a lead body, the pitch angle of the wire conductors decreases, thus disadvantageously resulting in flatter pitch and reduced flex life. In response to this problem with flex life, straight miniature cables were used as wire conductors. However, while the flex life of the wire conductors improved with miniature cables, problems again arose with the straight miniature cable pulling or tugging at the connection between the cable and the electrode contact, and the connection between the cable and the pulse generator. A solution to these problems is disclosed in the present invention.

SUMMARY OF THE INVENTION

The present invention recognizes and provides a solution to the problems of straight and coiled wire lead bodies in providing a unique medical lead that allows flexing in a straight wire lead body.

Accordingly, an object of the present invention is to provide for a unique implantable medical lead that permits flexing in a straight wire lead body and prevents loading of the electrode contacts of the medical lead or pulse generator.

The present invention provides an implantable medical lead for spinal cord, deep brain or peripheral nerve stimulation comprising, in the preferred embodiment, a wire lead body defining a sigma deformable shape and a plurality of electrode contacts coupled to the lead body at the distal end of the lead. The medical lead at its proximal end may be coupled to an implantable pulse generator, additional, intermediate wiring, or other stimulation device. The plurality of electrode contacts provides electrical stimulation to targeted human tissue.

In use, the medical lead and the implantable pulse generator are anchored in their desired positions either mechanically or due to eventual scarring. The lead body of the present invention, which defines a sigma shape, couples the electrode contacts and pulse generator. Advantageously, the sigma shape of the wire lead body permits flexing of the lead body when a patient shifts or moves around. Further, the sigma shape of the lead body flexes or stretches without pulling on or loading either the anchored electrode contacts or the anchored pulse generator. In addition, the sigma shaped lead body of the present invention can replace the coiled wire lead bodies when the pitch of the coil lowers the flex life unacceptably or, alternatively, the sigma shaped lead body can be used with the coiled wire lead bodies and provide additional relief in the form of increased flex life to such lead bodies.

The full range of objects, aspects and advantages of the invention are only appreciated by a full reading of this specification and a full understanding of the invention. Therefore, to complete this specification, a detailed description of the invention and the preferred embodiment follows, after a brief description of the drawing.

BRIEF DESCRIPTION OF THE DRAWING

The preferred embodiment of the invention will be described in relation to the accompanying drawing. In that drawing, the following figures have the following general nature.

In the accompanying drawing, like reference numbers are used throughout the various figures for identical structures.

DESCRIPTION OF THE PREFERRED EMBODIMENTS

Figure 1:
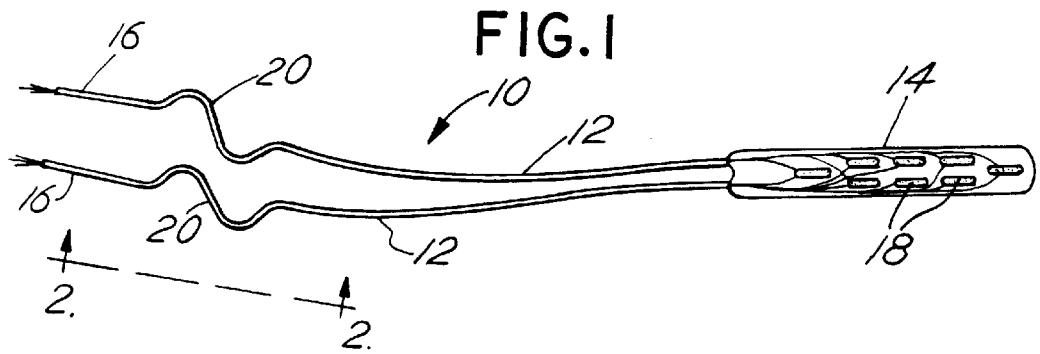
FIG. 1 is a plan view of the lead with sigma feature of the present invention.

Referring to FIG. 1, a medical lead 10 for spinal cord, deep brain and peripheral nerve stimulation comprises at least one lead body 12 and a lead paddle 14 coupled at one end to the lead body. The lead body 12 further comprises at least one wire conductor. The number of wire conductors may be increased to two, three, or more, dependent on need unrelated to this invention and significant generally to the number of electrical signals to be generated.

Each proximal end 16 of a lead body such as the illustrated lead bodies 12 may be coupled to an implantable neurological pulse generator, additional, intermediate wiring, or other stimulation device. An example of such a neurological pulse generator is the ITREL II system from Medtronic, Inc., Minneapolis, Minn. The stimulation pulses produced by the implantable neurological pulse generator are carried from the pulse generator through the proximal ends 16 of the lead bodies 12 of the present invention through a sigma segment, to be described, to distal ends of the lead bodies 12, and thereby to a coupled lead paddle 14 having at least one electrode contact 18.

The lead paddle 14 of the preferred embodiment has a plurality of electrode contacts 18 arrayed along the length and across the width of the lead paddle 14. Varieties of alternate arrays and numbers of electrode contacts are contemplated. Explanation of the reasoning for specific arrays and numbers of electrode contacts is beyond this invention.

One or more of the electrode contacts 18 on the lead paddle 14 transmit the stimulation pulses to targeted human tissue. As preferred, the illustrated structure transmits stimulation pulses from a pair of the electrode contacts 18. The pair is selected through testing of the efficacy of alternate electrode pairs. Alternatively, the illustrated structure may transmit stimulation pulses from one electrode contact 18 or a plurality of electrode contacts 18 depending on the desired stimulation.

Though the preferred embodiment employs fully implantable elements, systems employing partially implanted generators and R-F coupling may also be used in the practice of the present invention. Such systems are also available from Medtronic, Inc., to under the trademarks X-trel and Mattrix.

Each lead body 12 of the present invention comprises one or more metal conductor wire(s) within an insulating sheath. As most preferred, the insulating sheath is formed of an inert material such as polyurethane.

Centrally, each lead body 12 has and defines a preferred deformable sigma segment or shape 20 lying in a plane. The sigma segment 20 may as desired be located at any position along the lead body 12. It is preferred that the sigma segment 20 be located near the distal or proximal end of the lead body 12. It is also within contemplation that the lead body may incorporate a plurality of adjacent or spaced sigma segments 20 in a single or multiple planes, or within the limits of each segment 20, in a helical or other form. Most preferably, each lead body 12 includes one sigma section 20. As illustrated and also as most preferred, each sigma section 20 is formed only of the lead body 12, as will be explained. Also as illustrated and most preferred, each sigma section 20 includes and consists of at least two longitudinally alternating and laterally opposed half-sigma sections. Each such half-sigma section has essentially a half-sine wave configuration and shape, such that the whole sigma section has essentially a full sine wave configuration and shape, beginning and ending with the line defined by the general shape of the lead body 12 as the base line. Thus, a first half-sigma section extends laterally in a first direction from the conductor base line and returns to the base line, thereby forming a half-loop. A second half-sigma section extends from the first half-sigma section in the opposite lateral direction from the first half-sigma section. The second half-sigma section also returns to the base line, thereby forming a second half-loop. Combinations of more sigma sections 20 or deeper sigma sections 20 are contemplated and within the scope of this invention.

Figure 2:
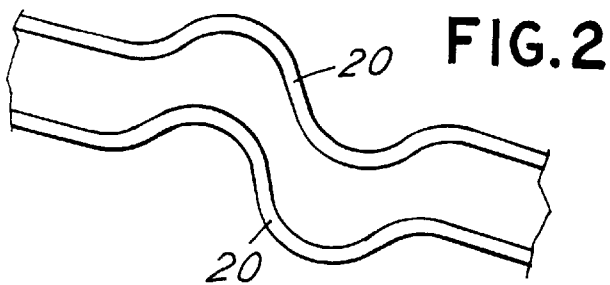
FIG. 2 is a view similar to FIG. 1 showing the ability of the invented lead to flex or stretch in the sigma area of the lead.

Advantageously, the sigma section 20 of the otherwise straight lead body 12 provides flexing and stretching of the straight lead body when loads are applied at either end of the straight wire. That is, when a patient with an implantable medical lead 10 of the present invention moves or bends, the sigma shape 20 of the lead body 12 flexes or stretches and allows the implanted lead paddle 14 to remain as positioned relative to the body of the patient. The lead paddle 14 will be able to move or bend with the patient relative to the external world substantially completely without placing a load on the connection between the wire conductor and the electrode contact of the lead paddle 14, or the opposed pulse generator. Thus, the sigma segment 20 flexes or stretches before any loading on the wire-electrode connection of the lead paddle 14 or the wire connection to the implantable pulse generator. With the most preferred, sine-wave sigma section 20 as illustrated, stretching or flexing of the sigma segment 20 occurs by lengthening of the sigma segment, as in FIG. 2. Both areas of the lead body 12 adjacent the ends of the sigma segment remain in lateral position relative to the body, as the sigma section flattens and lengthens.

Moreover, as constructed, each sigma segment 20 resiliently returns to its original sigma shape after patient moving or bending terminates and the patient moves or bends to their original position. That is, in a free state, the sigma segment 20 can resiliently return to its original shape after flexing or stretching of the lead body. For this purpose, the sigma segments are constructed as follows. With a pre-existing lead body which is completely straight, insofar as matters, the lead body in the area of the desired sigma segment is placed in a mold having the desired sigma shape as the channel of the mold. The mold and included lead body segment is then brought through a combination of elevated temperature and time such that the material of the insulating sheath softens and when returned to room temperature, takes the sigma shape of the mold channel without significant degradation of the material of the sheath. For a variety of materials, a variety of combinations of temperature and time are possible and contemplated. The material used for the lead body will not soften nor reflow at body temperature.

Additionally, the sigma shape 20 performs the same function of a helical wire, while at the same time, providing the advantages of lower electrical resistance of straight wires. Further, a lead body 12 with the sigma feature may consist of any suitable biocompatible and/or biostable conductor material and may be insulated with any suitably flexible outer surrounding sheath. Thus, the internal wire and surrounding sheath are both formed of materials which do not require forces in excess of those caused by movement of the parts of the human body to cause the sigma segment to lengthen and flatten. In contrast, and as with common materials of such structures, the internal wire and surrounding sheath are of materials such that the forces of muscular movement of parts of the human body cause flexing of sigma segments.

Figure 3:
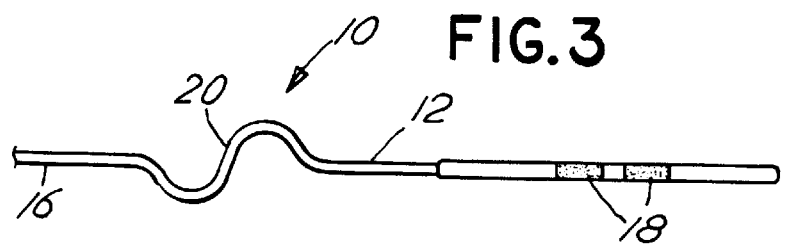
FIG. 3 is a plan view of a percutaneous lead with the sigma feature of the present invention.
Figure 4:
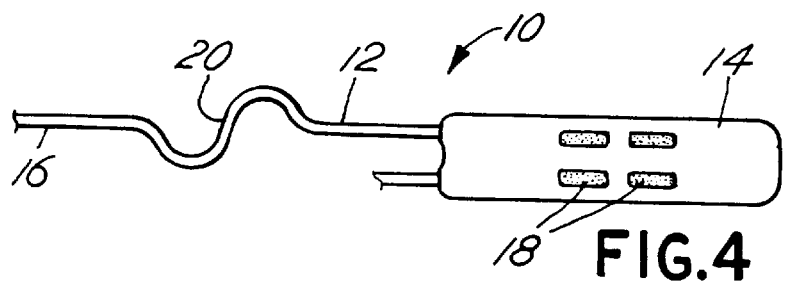
FIG. 4 is a plan view of a surgical lead having a lead paddle and the sigma feature of the present invention.

Referring to FIG. 3, the medical lead 10 of the present invention may be a percutaneously inserted lead having a plurality of electrode contacts or, as illustrated in FIG. 4, a surgical lead having a lead paddle 14. As above, the lead paddle 14 has a plurality of electrode contacts 18, such as an array, for transmitting stimulation signals to surrounding human tissue. The implantable pulse generator provides respective stimulation signals having specified signal parameters to selected of the contacts 18 in the array. Thus, depending on the desired location and parameters of the stimulation signal parameters of the stimulation signals can be controlled and directed to selected electrical contacts for targeted stimulation.

The electrode contacts of either the lead paddle or the percutaneous lead are properly positioned as known as a result of fluoroscopy and trial stimulation of tissue. To allow placement of a percutaneous medical lead body in the general area in which stimulation is desired, and within which, selection from among the multiple electrical contacts allows for refined tissue targeting, the sigma segment is adequately flexible to fit through a Tuohy needle through which the percutaneous lead body is to be introduced to the human body. In addition, the sigma segment flexably straightens when a temporary stylet is inserted in the center lumen of the lead body. That is, a Tuohy needle and a lead body stylet may be employed to introduce the percutaneous lead body having the preferred sigma segment to the targeted stimulation area of the human body. After removal of the needle and lead body stylet, the sigma segment will return to a sigma shape. The sigma segment then remains at rest until bodily movements occur, or until physician manipulation of the lead bodies tugs on the lead bodies. In a sense, the sigma segment constitutes and provides a resilient or spring means for providing longitudinal separating movement essentially free of lateral movement of the outer ends of the sigma segment. This function of the sigma segment advantageously allows the electrode contacts and pulse generator to move independent of each other without loading the connection between the wire conductors and the electrode contacts or the wire conductors and the pulse generator.

The preferred embodiments of the invention are now described as to enable a person of ordinary skill in the art to make and use the same. Variations of the preferred embodiment are possible without being outside the scope of the present invention. Therefore, to particularly point out and distinctly claim the subject matter regarded as the invention, the following claims conclude the specification.

What is claimed is:

1. An implantable medical lead for electrical stimulation, the medical lead having electrode contacts and metal wires connected to the electrode contacts, comprising:

a lead body having a distal end and a proximal end, the lead body defining at least one substantially planar deformable sigma segment, whereby the substantially planar deformable sigma segment of the lead body provides flexible longitudinal extension of the lead body and thereby substantially prevents loading of the electrode contacts during the experiencing of forces tending to load the electrode contacts.

2. An implantable medical lead as in claim 1, wherein the proximal end of the lead body is structured to be couplable to an implantable pulse generator.

3. An implantable medical lead as in claim 1, wherein the lead body includes an outer insulating sheath surrounding the metal wires.

4. An implantable medical lead as in claim 1, wherein the deformable sigma segment of the lead body constitutes and provides a resilient sigma segment means for providing longitudinal separating movement essentially free of lateral movement of outer ends of the sigma segment, and resilient return to original longitudinal spacing of the outer ends.

5. An implantable medical lead as in claim 1, wherein the sigma segment includes two opposed, interconnected half-sigma sections.

6. An implantable medical lead as in claim 1, wherein the deformable sigma segment of the lead body is constructed of materials such that the sigma segment flexes before loading on the electrode contacts or pulse generator.

7. An implantable medical lead as in claim 1, wherein the lead body defines a plurality of deformable sigma segments.

8. An implantable medical lead as in claim 1, further defining a plurality of lead bodies having sigma deformable shapes.

9. An implantable medical lead for electrical stimulation, comprising:

a plurality of lead bodies including substantially planar sigma segments, and a lead paddle coupled to the lead bodies, the lead paddle having a plurality of electrode contacts and metal wires connected to the plurality of electrode contacts, the substantially planar sigma segments providing flexing and thereby preventing loading of the electrode contacts of the lead paddle.

10. An implantable medical lead as in claim 9, wherein the plurality of lead bodies include sigma segments at essentially the same distance from the lead paddle.

11. An implantable medical lead as in claim 9, wherein the plurality of lead bodies define a plurality of spaced sigma segments in each lead body.

12. An implantable medical lead as in claim 9, wherein the plurality of lead bodies include electrically insulating outer sheaths surrounding the metal wires.

13. An implantable medical lead as in claim 9, wherein the plurality of sigma segments constitute and provide resilient sigma segment means for providing longitudinal separating movement essentially free of lateral movement of outer ends of the sigma segments, and resilient return to original longitudinal spacing of the outer ends.

14. An implantable medical lead as in claim 9, wherein the plurality of sigma segments each include at least one half-sigma section.

* * * * *

UNITED STATES PATENT AND TRADEMARK OFFICE

Certificate

Patent No. 6,066,165

Patented: May 23, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Gabor B. Racz, Lubbock, TX (US); and Thomas E. Cross, Jr., St. Francis, MN (US).

Signed and Sealed this Twenty-Ninth Day of July 2008.

BRIAN L. CASLER
*Supervisory Patent Examiner*
Art Unit 3737